(12) United States Patent  
Linares

(10) Patent No.: US 9,033,985 B2
(45) Date of Patent: May 19, 2015

(54) COMPOSITE AND SURFACE MOUNTED BRACE, KIT AND ASSEMBLY FOR SUPPORTING A FRACTURED BONE

(71) Applicant: Linares Medical Devices, LLC, Auburn Hills, MI (US)

(72) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 246 days.

(21) Appl. No.: 13/671,848

(22) Filed: Nov. 8, 2012

(65) Prior Publication Data

US 2013/0197520 A1    Aug. 1, 2013

Related U.S. Application Data

(63) Continuation-in-part of application No. 12/434,089, filed on May 1, 2009, now abandoned.

(60) Provisional application No. 61/049,507, filed on May 1, 2008.

(51) Int. Cl.

| | | |
|---|---|---|
| *A61B 17/82* | (2006.01) | |
| *A61B 17/16* | (2006.01) | |
| *A61B 17/68* | (2006.01) | |
| *A61B 17/72* | (2006.01) | |
| *A61B 17/84* | (2006.01) | |

(52) U.S. Cl.
CPC .............. *A61B 17/82* (2013.01); *A61B 17/1615* (2013.01); *A61B 17/1617* (2013.01); *A61B 17/68* (2013.01); *A61B 17/72* (2013.01); *A61B 17/842* (2013.01); *A61B 17/846* (2013.01)

(58) Field of Classification Search
CPC ................... A61B 2019/2246; A61B 17/7053; A61B 17/7065; A61B 17/7068; A61B 17/707; A61B 17/842
See application file for complete search history.

(56) References Cited

U.S. PATENT DOCUMENTS

| | | | |
|---|---|---|---|
| 4,553,535 | A | 11/1985 | Finnieston et al. |
| 4,778,468 | A | 10/1988 | Hunt et al. |
| 4,805,606 | A | 2/1989 | McDavid, III |
| 5,286,249 | A | 2/1994 | Thibodaux |
| 6,149,651 | A | 11/2000 | Drewry et al. |
| 6,159,210 | A | 12/2000 | Voor |
| 6,413,259 | B1 | 7/2002 | Lyons et al. |
| 7,001,389 | B1 | 2/2006 | Navarro et al. |
| 7,090,676 | B2 | 8/2006 | Huebner et al. |
| 7,153,309 | B2 | 12/2006 | Huebner et al. |

(Continued)

*Primary Examiner* — David Isabella
*Assistant Examiner* — Ann Schillinger
(74) *Attorney, Agent, or Firm* — Gifford, Krass, Sprinkle, Anderson & Citkowski, P.C.

(57) ABSTRACT

A brace for supporting an exterior surface of a damaged bone including a plurality of elongated members interconnected at each of intermediate overlapping and end-to-end locations. An additional pair of end disposed supports is pivotally interconnected to outermost of the elongated interconnected members. A pair of elongated ties seating through apertures formed in the end disposed supports. The brace is adapted to being placed in encircling fashion over the damaged bone, following which the ties are displaced relative to at least one of the end disposed supports in order to cause the elongated members to inter-extend in scissor-like fashion in order to tighten the brace against the bone and to apply a preferred degree of compressive and immobilizing force around the damaged exterior bone.

5 Claims, 12 Drawing Sheets

(56) References Cited

U.S. PATENT DOCUMENTS

| | | |
|---|---|---|
| 7,179,260 B2 | 2/2007 | Gerlach et al. |
| 7,250,054 B2 | 7/2007 | Allen et al. |
| 7,255,701 B2 | 8/2007 | Allen et al. |
| 7,273,481 B2 | 9/2007 | Lombardo et al. |
| 7,341,589 B2 | 3/2008 | Weaver et al. |
| 2004/0260287 A1* | 12/2004 | Ferree .................... 606/61 |
| 2005/0107796 A1 | 5/2005 | Gerlach et al. |

* cited by examiner

FIG. 11
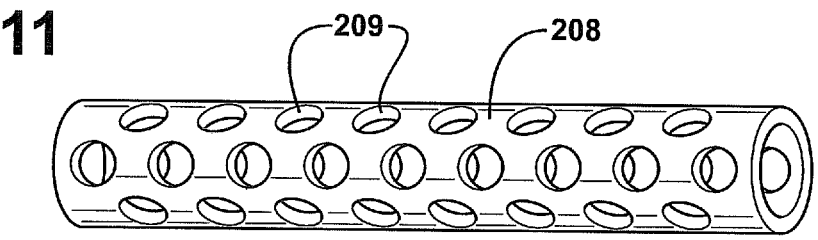
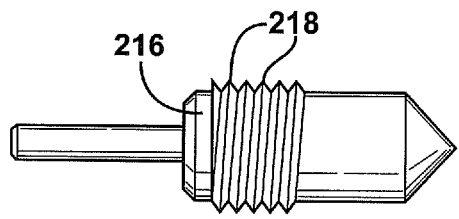
FIG. 12A
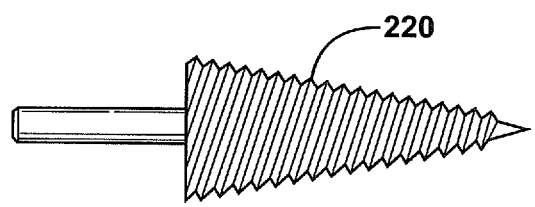
FIG. 12B
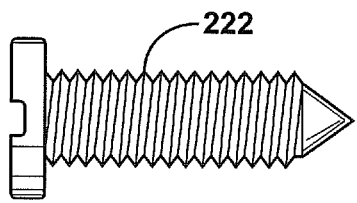
FIG. 13A
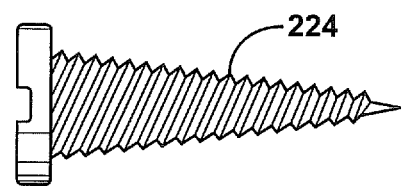
FIG. 13B
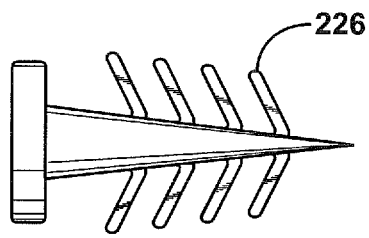
FIG. 13C
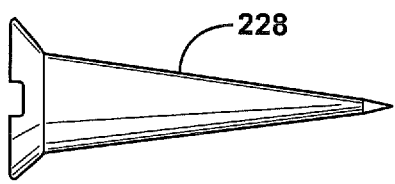
FIG. 13D
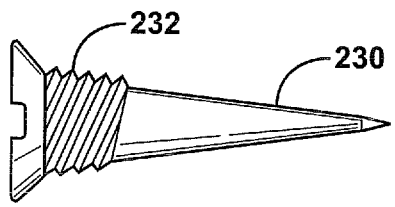
FIG. 13E

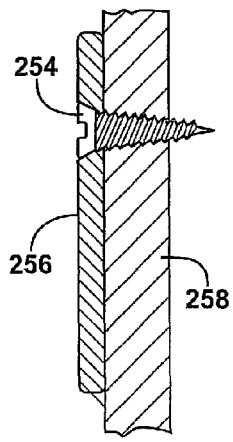
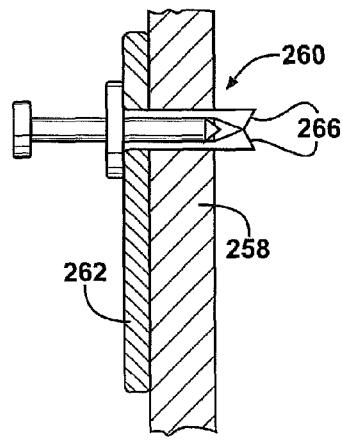
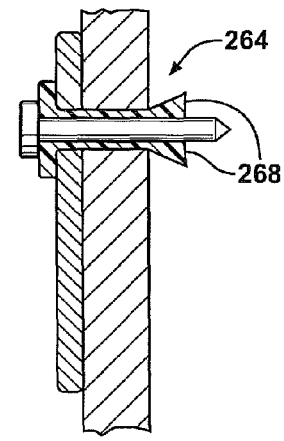
FIG. 17A  FIG. 17B  FIG. 17C
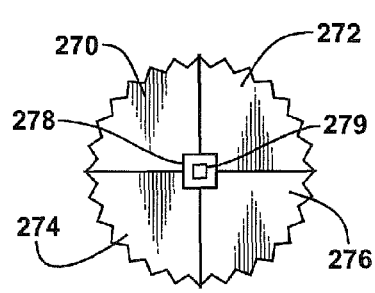
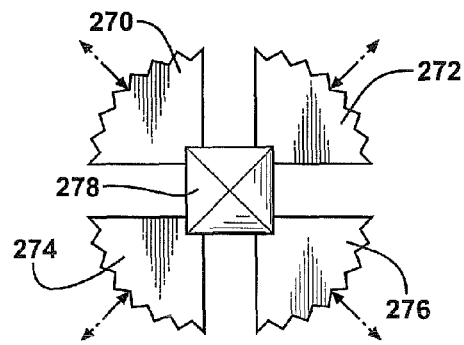
FIG. 18A
FIG. 18B
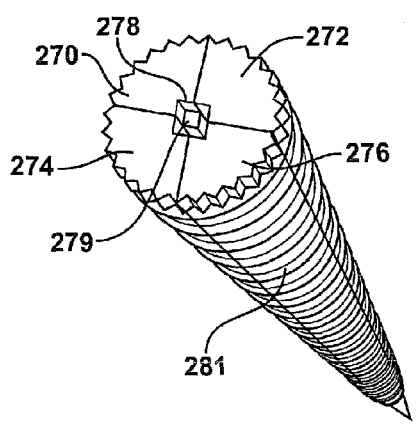
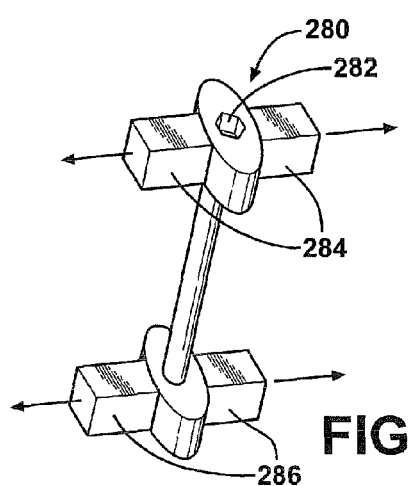
FIG. 18C  FIG. 18D

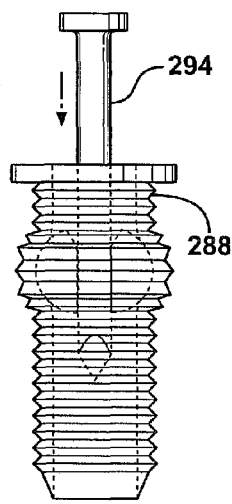
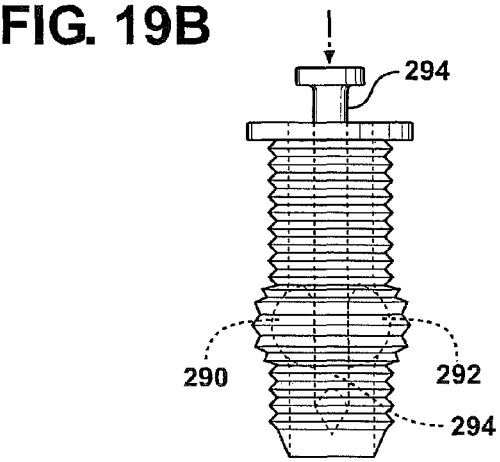
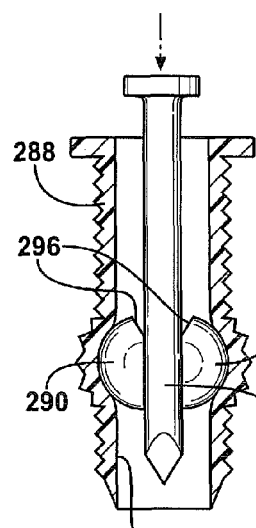
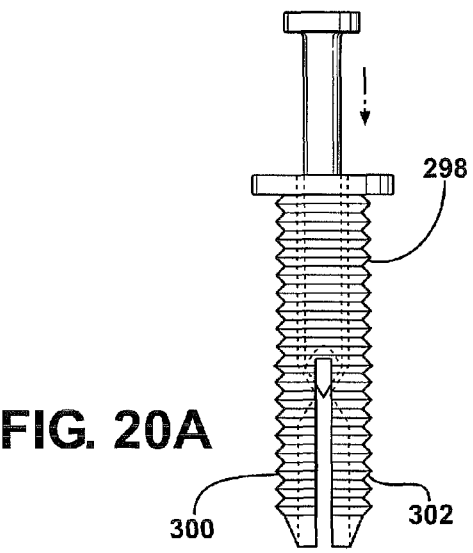
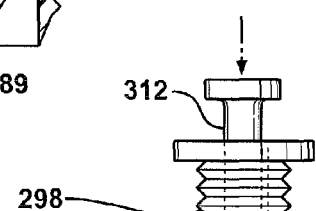
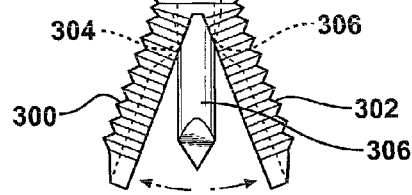
FIG. 19A
FIG. 19B
FIG. 19C
FIG. 20A
FIG. 20B

US 9,033,985 B2

COMPOSITE AND SURFACE MOUNTED BRACE, KIT AND ASSEMBLY FOR SUPPORTING A FRACTURED BONE

CROSS-REFERENCE TO RELATED APPLICATIONS

This Application is a continuation-in-part of U.S. Ser. No. 12/434,089, filed May 1, 2009, which in turn claims the benefit of U.S. Provisional Application 61/049,507 filed on May 1, 2008.

FIELD OF THE INVENTION

The present invention discloses a brace, kit and associated assembly for securing about an exterior surface of a cracked or fractured bone. According to one series of related variants, the braces can take the form of one or more encircling plastic ties or cables, between which are supported a plurality of circumferentially spaced, selectively overlapping and/or circumferentially displaceable plastic or other constructed supports.

BACKGROUND OF THE INVENTION

Bone plate and screw assemblies are known in the prior art, such as for use in securing a bone sprain or fracture. Also known is the provision of bone screws for securing the plate such as in overlaying fashion relative to the sprain or fracture location.

Representative prior art references directed to various types of bone plate and screw assemblies include such as those depicted in U.S. Pat. No. 6,413,259 to Lyons et al. U.S. Pat. No. 7,273,481 to Lombardo, U.S. Pat. No. 7,179,260 to Gerlach, U.S. Pat. No. 7,090,676 to Huebner, and U.S. Pat. No. 7,001,389 to Navarro.

U.S. Pat. Nos. 7,255,701 and 7,250,054, both to Allen, teach a system, method and apparatus for clamping and reclamping an orthopedic surgical cable used with an orthopedic implant device. Voor, U.S. Pat. No. 6,159,210, teaches a fixation pin for attaching an immobilizing device or frame to a bone or to the skull of a patient. Finally, U.S. Pat. No. 7,153,309, to Huebner, teaches a system and kit for guiding a hole forming tool and/or fastener through a bone and to a connected bone-repair device.

SUMMARY OF THE INVENTION

The present invention discloses a brace for supporting an exterior surface of a damaged bone which includes a plurality of elongated members each having a flattened shape. The elongated members are interconnected at each of intermediate overlapping and end-to-end locations. An additional pair of end disposed supports is pivotally interconnected to outermost of the elongated interconnected members. A pair of elongated ties seating through apertures formed in the end disposed supports.

In use, the brace is adapted to being placed in encircling fashion over the damaged bone, following which the ties are displaced relative to at least one of the end disposed supports in order to cause the elongated members to inter-extend in scissor-like fashion in order to tighten the brace against the bone and to apply a preferred degree of compressive and immobilizing force around the damaged exterior bone.

A related variant of the scissor brace incorporates first and second sub-pluralities of crosswise elongated members extending between the end disposed supports. An intermediate support is positioned between the end disposed supported and to which the sub-pluralities of crosswise elongated members are additionally pivotally engaged. In either variant, at least one lengthwise extending slot is defined in each of the end disposed supports, within which a selected pivotal end mounting location of an elongated member is seated for providing a degree of combined translating and pivotal motion of the selected crosswise elongated (scissor) members relative to the end disposed supports.

BRIEF DESCRIPTION OF THE DRAWINGS

Reference will now be made to the attached drawings, when read in combination with the following detailed description, wherein like reference refer to like parts throughout the several views, and in which:

FIG. 11 is an illustration of the insert and which can be constructed of a composite and hardened plastic material;

FIG. 12A is an illustration of a first configuration of bone drill bit utilized in the anchoring of a mounting screw and incorporating a fluted section along an intermediate length of the shaft;

FIG. 12B is an illustration of a reamer type bit according to a second configuration;

FIGS. 13A-13E illustrate a variety of anchor screws exhibiting varying fluted and spike patterns;

FIG. 17A is a side cutaway illustration of a mounting screw for mounting a brace plate to a surface of a bone;

FIG. 17B is a further illustration of a modified anchor and deformable spacer for mounting a brace plate to a bone;

FIG. 17C is a yet further illustration of a modified anchor and plastic spacer according to a further variant;

FIG. 18A is an end view of a laterally displaceable anchoring screw according to a further preferred embodiment;

FIG. 18B is a succeeding end view illustrating individual and linearly extending portions of the anchoring screw outwardly displaced relative to a central supporting stem;

FIG. 18C is a perspective illustration of the anchoring screw illustrated in FIG. 18A;

FIG. 18D is a further variation of a laterally displaceable anchor and which include first and second individually outwardly displaceable ends;

FIG. 19A is a further illustration of an anchoring screw and which incorporates a plasticized sleeve within which are disposed a pair of internal passageway proximate and laterally displaceable undercut engaging portions;

FIG. 19B is a succeeding illustration to that shown in FIG. 19A and depicting the undercut engaging portions laterally outwardly bulged in response to the inwardly engagement of the anchoring screw;

FIG. 19C is a transparent view of the anchoring sleeve and illustrating both the configuration of the laterally displaceable undercut engaging portions, as well as the deformable properties associated with the locations of the sleeve overlaying the undercut portions;

FIG. 20A is an illustration of a modified version of anchoring screw and which exhibits a reconfigured sleeve with first and second end extending and laterally displaceable portions;

FIG. 20B is a cutaway view of the anchoring screw shown in FIG. 20A and illustrating one possible configuration of linkage for causing outwardly lateral deflection of the end extending sleeve portions in response to inward engagement of the associated spike;

DETAILED DESCRIPTION OF THE PREFERRED EMBODIMENTS

Referring now to the various illustrations, the present invention discloses a plurality of embodiments for bracing or otherwise supporting a damaged exterior bone location. As will be subsequently described, the present invention discloses a series of related variants associated with the brace, kit and assembly, these including one or more encircling plastic ties or cables, between which are supported a plurality of circumferentially spaced, selectively overlapping and/or circumferentially displaceable plastic supports.

Additional variants include linear extending plastic supports which can be anchor secured to an exterior cracked or fractured surface of a bone by clips, rivets or resistive biasing and serrated edged zip strips to the damaged bone exterior. A further variant provides an insert configured for insertion with the hollow interior of the bone and in order to function as a permanent internal splint.

Figure 1:
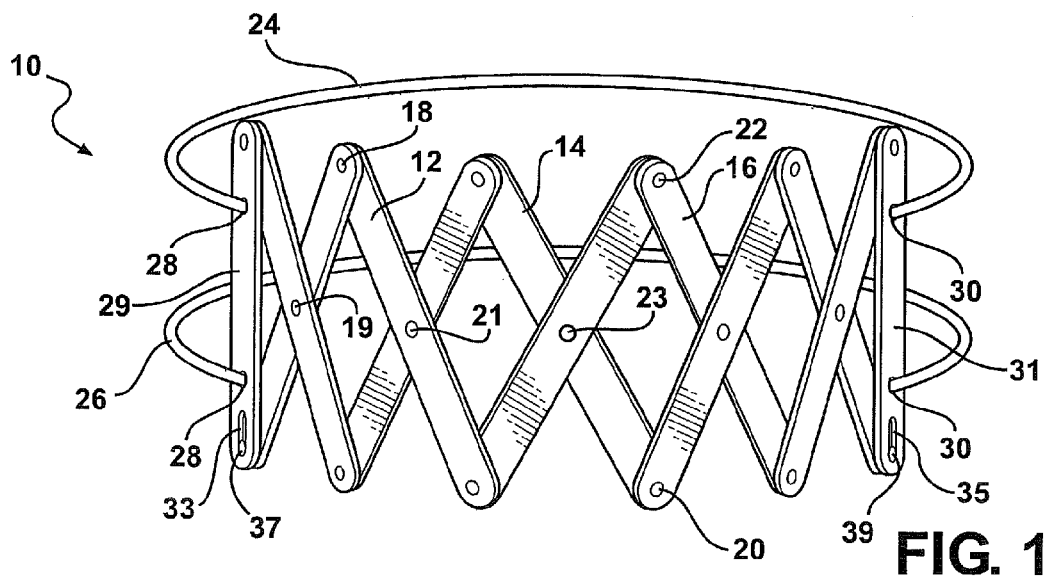
FIG. 1 is a perspective view of a damaged bone securing brace according to a first embodiment of the present invention and exhibiting a pair of encircling plastic ties or cables, between which are supported a plurality of circumferentially spaced, overlapping and circumferentially displaceable plastic supports.

Referring first to FIG. 1, a perspective illustration is shown at 10 of a brace according to a first embodiment of the present inventions and which is utilized for supporting about a damaged location of a patient's bone (e.g. sprain, crack or fracture). A plurality of circumferentially spaced, overlapping and circumferentially displaceable plastic supports, see at 12, 14, 16, et. seq. are provided and which are pivotally interengaged relative to one another such as by end-hinged or collar supported locations, see as further shown at 18, 20, 22 et. seq.

The supports 12, 14, 16, et seq. each further exhibit a generally flattened and elongate planar shape and are additionally pivotally interengaged at intermediate overlapping locations 19, 21, 23, et. seq., these in addition to the end-hinged overlapping connections (see again upper hinged connection 18 and 22 and lower representative hinged locations 20). The elongate and planar shaped supports are constructed from such as a composite plastic, although it is also understood that the material construction can include any of a high grade steel/composite steel and/or optional carbon fiber/graphite material.

A pair of encircling plastic ties or cables are shown at 24 and 26, these extending through pairs of apertures 28 and 30 associated with outermost and opposite end disposed supports 29 and 31, between which extend and are interconnected the plurality of pivotally displaceable supports. As further clearly shown in FIG. 1, at least one lengthwise extending slot is defined in each of said end disposed supports (at 33 for support 29 and further at 35 for further support 31), within which a selected pivotal end mounting location (pins 37 and 39) of outermost of the scissor interconnected elongated members are seated in order provide a limited degree of sliding displacement to the selected elongated members in combination with the pivotal articulation and as clearly evident.

Figure 2:
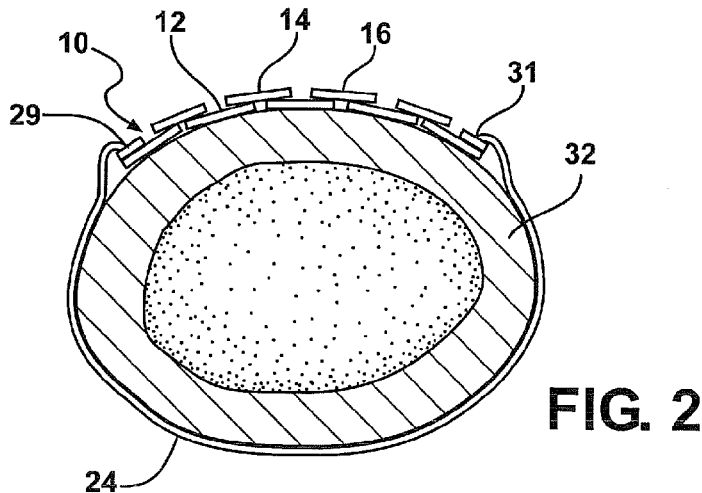
FIG. 2 is an overhead environmental view of the brace according to FIG. 1 in an installed configuration about a bone.

As further shown in the overhead view of FIG. 2, and upon installation about an exterior periphery of a bone 32, the individual supports are displaced in a generally scissor-like fashion in order to establish a desired degree of peripheral resistance about the exterior surface of the bone, and while shaping the brace 10 to conform to the bone surface, this further assisting in providing a desired degree of bracing support in both circumferential and lineal extending fashion. In order to maintain the brace 10 in a desired arrangement with the bone surface (at 32 in FIG. 2) anchoring pins or the like can be incorporated into the pivotally engaging and overlapping locations. The planar shaped supports can also be reconfigured (not shown) so that, upon pivoting to a desired inter-relationship the planar supports can be locked in position in order to maintain a desired compressive bias about the cracked or fractured bone.

It is further understood that the scissor-like supports can exhibit ratchet-tightening aspects, such as which can be configured upon overlapping faces of the scissor portions to enable the brace 10 to be tightened, this following initial positioning about the bone, to a final desired compressive arrangement. Such ratchet adjustable tightening features can enable the brace to be selectively tightened and loosened without the requirement of anchor fastening or the like.

As will be described in reference to subsequent embodiments, the straps 24 and 26 can further be secured to the outermost positioned of the linear extending supports 29 and 31, with inserting ends of the plastic cables being selectively tightened/loosened relative to the outermost positioned end supports 29 and 31 of the brace assembly (such as further occurring at underside mounting surfaces of the end supports 29 and 31 not shown in FIG. 1) in order to apply a preferred degree of compressive and immobilizing force around a damaged exterior bone location.

Figure 3:
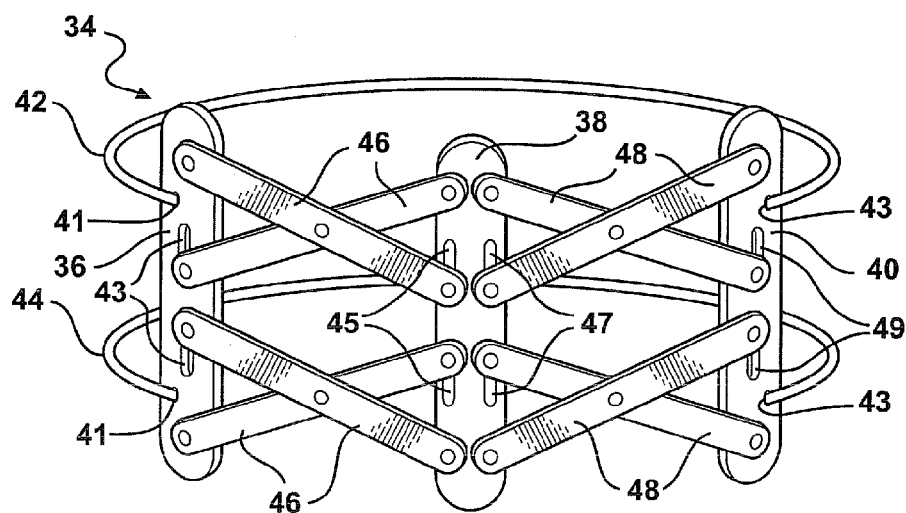
FIG. 3 is a perspective view of a brace according to a further preferred embodiment, and by which a plurality of tie or cable secured supports are interengaged in circumferentially displaceable fashion along the cables by pluralities of crosswise extending scissor portions.

Referring now to FIG. 3, a perspective view is shown at 34 of a brace according to a further preferred embodiment, and by which a plurality of tie or cable secured elongated supports are provided, see at 36, 38 and 40, and which are interengaged in peripherally supported and circumferentially displaceable fashion along opposite mounting ends of selected straps or cables, at 42 and 44. Pluralities of crosswise extending and inter-engaging scissor portions. at 46 and 48, provide pivotal displacing support between the planar shaped and spaced apart supports 36-40.

As in the variant of FIGS. 1-2, lengthwise slots can be provided in extended fashion along each of the of the supports 36, 38 and 40, this including a first pair of slots 43 depicted along support 36 for seating pin mounting locations of a selected pair 46 of crosswise scissor portions, with additional pairs of slots 45 and 47 depicted along middle extending support 38 for seating intermediate engaging pin ends of slots 46 and 48, and a further pair of lengthwise slots 49 for seating opposite pin ends of the selected pair of scissor portions 48. In this fashion, the scissor brace 34 provides an enhanced degree of combined linearly translating and pivotally articulating motion during installation and tightening around the damaged bone location (see also further exemplary depictions of damaged bone addressed by some form of externally mounted brace and as shown by example in each of FIGS. 4, 5C, 6B and 9C).

As with the embodiment 10 in FIG. 1, the straps/cables 42 and 44 can be tightened, such as again by opposite ends of the cables displacing through apertures (see pairs of apertures at 41 and 43 for outermost positioned supports 36 and 40), and thereby to apply a maximum desired degree of compressive surface force in cooperation with the scissor. The pairs of scissor portions can likewise incorporate the same locking or tightening aspects as disclosed in reference to the scissor portions in the brace 10 of FIG. 1.

Figure 4:
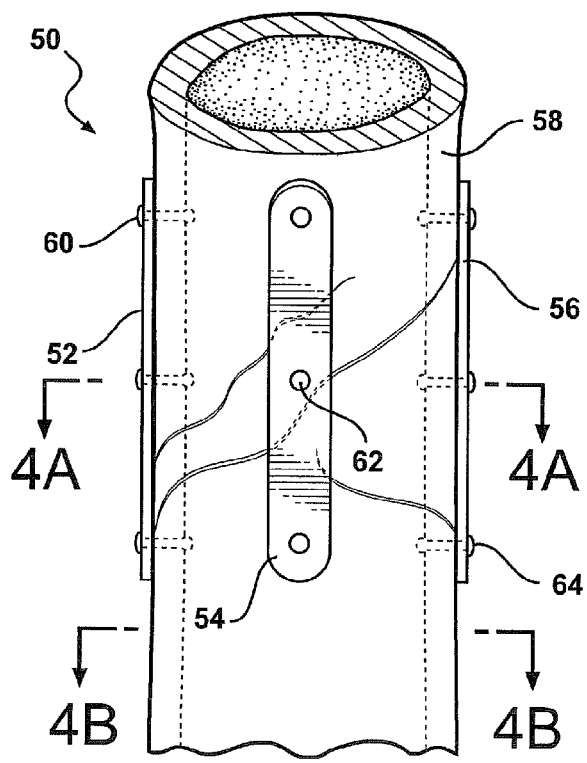
FIG. 4 is an environmental perspective of a plurality of linear extending plastic supports which can be anchor secured to an exterior cracked or fractured surface of a bone such as by clips or rivets.

Referring now to FIG. 4, an environmental perspective is shown at 50 of a further brace application in which a plurality of linear extending plastic supports 52, 54 and 56 are anchored or otherwise secured in individual peripherally spaced and linear extending fashion so as to overlay an exterior cracked or fractured surface of a bone 58. Anchoring of each elongated support is provided by such as inwardly engageable clips or rivets, this further being referenced by pluralities of rivets 60, 62 and 64 associated respectively with each of the linear extending plastic supports 52, 54 and 56. The rivets 60-64 as shown in FIG. 4 further exhibit an enlarged fastening head as well as an enlarged inner end for seating either within or against an enlarged machine undercut configured within the bone.

As will be described in additional detail throughout the succeeding embodiments, anchoring of the rivets includes the provision of appropriate medical drill technology, such as in order to machine mounting locations within the bone, this further contemplating employing the necessary machining technology in order to achieve the inwardly recessed and expanded profiles necessary for seating inner engaging rivet portions (see as also best shown by inner supporting rivet locations in FIG. 4A and which are located along inner defined annular surface locations of the bone in communication with inner marrow). The arrangement of FIG. 4 is most advantageously employed in situations where the surface cracks associated with the bone 58 extend in a generally combined circumferential and linear fashion, and further such that one or more of the anchored supports functions to secure and prevent the cracks from further propagating.

Figure 4A:
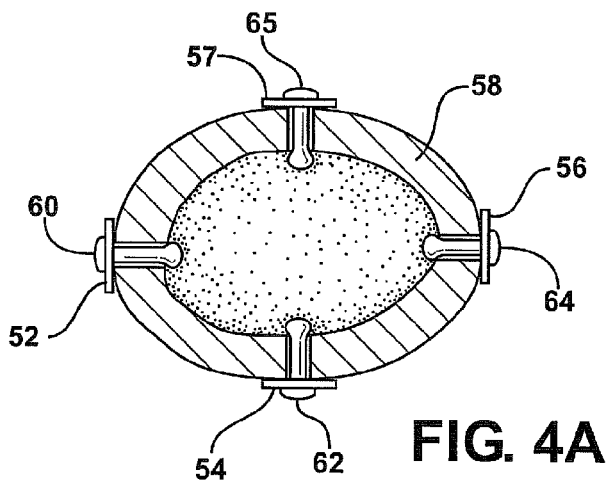
FIG. 4A is a first cutaway end view taken along Section 4A in FIG. 4 and illustrating the plurality of linearly anchored and circumferentially spaced apart plastic supports.
Figure 4B:
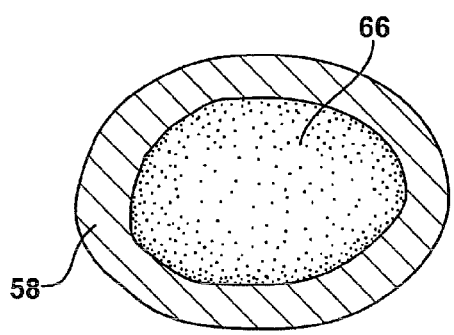
FIG. 4B is a second cutaway end view taken along Section 4B in FIG. 4 and showing a cross section of a bone with interior marrow supply.

Referring to FIG. 4A, a first cutaway end view taken along Section 4A in FIG. 4 illustrates the plurality of linearly anchored and circumferentially spaced apart plastic supports 52, 54, 56, et. seq. in combination with selected anchoring rivets 60, 62, and 64. An optional and fourth linear extending support 57 and associated rivet 65 is also shown, this being hidden from the illustration of FIG. 4. FIG. 4B is a second cutaway end view taken along Section B in FIG. 4B and showing a cross section of the bone 58 with interior marrow supply 66.

As best shown in the enlarged cutaway of FIG. 4A, and which will be further described in detail throughout the various succeeding embodiments, the configuration of the rivet 60, 62, and 64, is such that each includes an outer bulbous formed edge for abutting to a surface location of a previously drilled mounting hole within the bone. As previously referenced in FIG. 4, the rivets each further include an inner enlarged, e.g., bulbous portion, this seating within an inner undercut configuration (which again can be formed by the appropriate tooling) with either the inner bone marrow surface or, as will be further described in succeeding embodiments, can be undercut formed at an inner location associated with the bone wall thickness.

Figure 5:
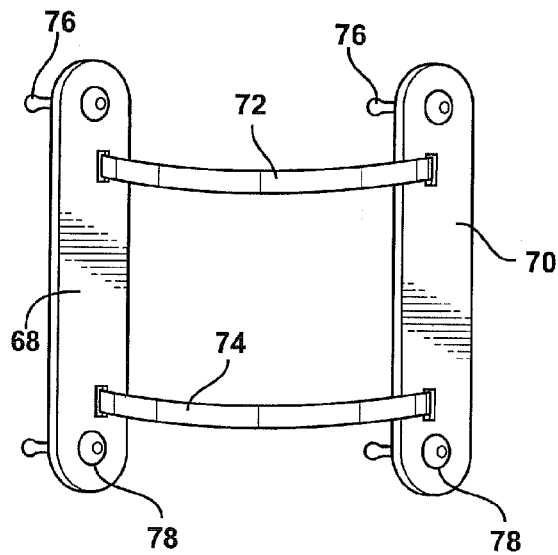
FIG. 5 is an illustration of a composite plastic support according to a further variant and which includes a pair of spaced apart plastic supports inter-engaged by a pair of crosswise extending supports.

Referring now to FIG. 5, an illustration is shown of a composite plastic support according to a further variant and which includes a pair of spaced apart plastic supports 68 and 70 inter-engaged by a pair of crosswise extending supports 72 and 74. As further shown in an end cutaway view in FIG. 5A, an associated environmental application of the support of FIG. 5 illustrates a pair of composite and interconnected plastic supports 68 and 70 secured along circumferentially displaced (or otherwise spaced) perimeter defined locations associated with a bone anchoring configuration.

Figure 5A:
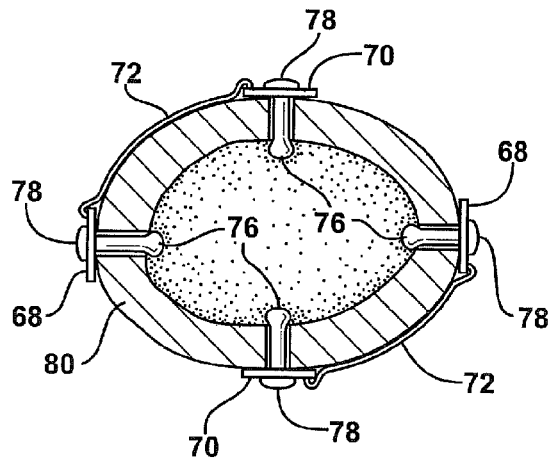
FIG. 5A is an end cutaway view of an environmental application illustrating a pair of composite plastic supports shown in FIG. 5 secured along opposite perimeter defined locations associated with a bone anchoring configuration.

Also shown in FIG. 5A, a plurality of individual rivets are provided for securing the spaced apart composite supports 68 and 70, each of the rivets including inner end positioned anchoring locations, as collectively referenced at 76 (these similar to the enlarged and bulbous inner ends associated with the rivets 60-64 in FIGS. 4 and 4A), as well as opposite outer end positioned anchoring locations, again collectively at 78. The rivets are placed in corresponding fashion at both upper and lower end or otherwise disposed engagement locations (e.g. preformed apertures) defined within the composite plastic supports and which secure within machined apertured or mounting locations associated with a bone 80, such as in a manner previously described.

Figure 5B:
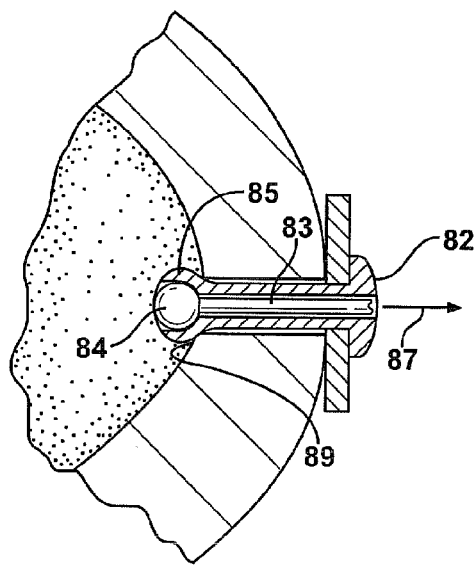
FIG. 5B is a sectional cutaway configuration of a plastic support anchor (e.g. rivet or clip) secured to a selected bone location.

Referring to FIG. 5B, an enlarged and sectional cutaway configuration is further shown of a plastic support anchor (e.g. rivet or clip) 82 secured to a selected bone location, and in a manner similar to that previously described with both inner and outer end displacing surfaces. Also illustrated in FIG. 5B is the provision of an optional graphite threaded portion, this shown at 83 and extending through an interior lineal extending location associated with the rivet 82 prior to terminating in an inner disposed spherical end 84.

An outer sleeve shaped portion associated with the rivet encircles the graphite threaded portion 83 and terminates in a surrounding covering, further shown at 85 disposed about the spherical end 84. Upon being displaceable in an outward direction, the spherical mounted end 84 "pinches" and subsequently deforms thereabout the annular covering 85, causing the outer covering 85 to encircle and abut the inner machined edge of the bone aperture (see at 89), thereby more permanently securing the same to the bone and so as to operate as an inner rivet location seating against an inner surface of the bone as a result of such deformation more effectively and completely covering the inner diameter of the machined bone aperture.

Figure 5C:
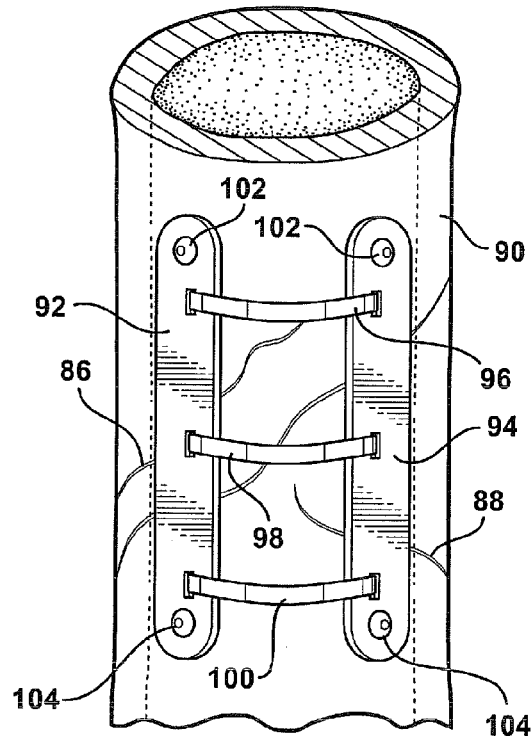
FIG. 5C is a further perspective illustration of a selected composite plastic support, such as shown in FIGS. 5 and 5A, secured to a damaged bone location.

FIG. 5C is a further perspective illustration of a yet further modified version of a composite plastic support, similar to that shown in FIGS. 5 and 5A, and which is secured to a damaged bone location depicted by fractures or cracks 86 and 88 defined in combined lineal and circumferential extending fashion along a bone 90. The composite supports again include a pair of spaced apart composite plastic supports or straps, see at 92 and 94, and which are inter-engaged by a plurality of three crosswise extending and reinforcing support bands 96, 98 and 100. Anchoring locations (upper ends) 102 and (lower ends) 104 are defined at the respective ends of the composite and elongated supports 92 and 94, again according to a fashion similar to that previously described (such as by rivets 60-64 in FIG. 4) and which are configured to receive such anchoring rivets in a fashion similar to that previously described.

Figure 6:
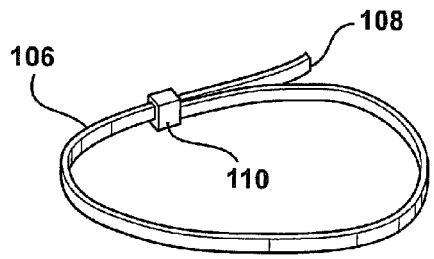
FIG. 6 is an illustration of an encircling plastic support strap with end trailing and circumferentially displaceable/tightening tail portion according to a further preferred embodiment.

Referring now to FIG. 6, an illustration is provided of an encircling (such as composite) plastic support strap 106, such as corresponding to any of the brace securing/supporting straps previously described and which exhibits an end trailing and circumferentially displaceable/tightening tail 108 portion according to a further preferred embodiment. The strap 106 is configured in a substantial loop configuration, with the tail 108 inserting through an end supported housing 110 exhibiting an interior slit or aperture location, this permitting the strap 106 to be installed about a bone 112 (see further FIG. 6A) and subsequently tightened, by linearly displacing the tail 108, such that the strap establishes a desired protective configuration about a damaged bone exterior in a diameter reducing manner.

Figure 6A:
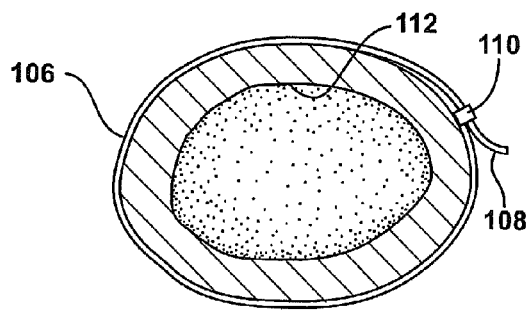
FIG. 6A is an end cutaway view of an environmental application illustrating the plastic support strap in FIG. 6 secured about an exterior perimeter surface of a damaged bone.
Figure 6B:
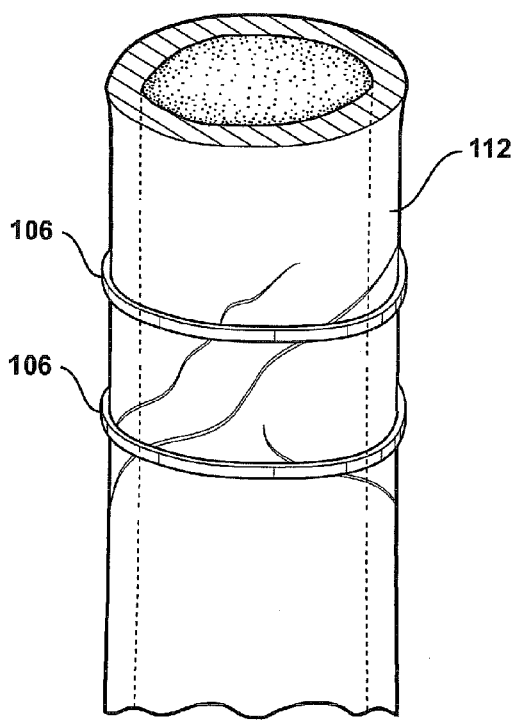
FIG. 6B is a successive perspective illustration of the assembly shown in FIG. 6A, and illustrating first and second plastic support straps peripherally secured and first and second linear spaced apart locations associated with the bone.

Reference is further made again both to the end cutaway view of FIG. 6A of an environmental application illustrating the plastic support strap in FIG. 6 secured about an exterior perimeter surface of a damaged bone, as well as the successive environmental perspective illustration in FIG. 6B of the assembly shown in FIG. 6A and illustrating first and second plastic support straps 106 peripherally secured and first and second linear spaced apart locations associated with the bone 112. It is also envisioned that the plastic support straps can exhibit a rip tie configuration and such that a serrated engagement is established between the aperture configured within the housing 110 and the inserting tail 108.

Figure 7:
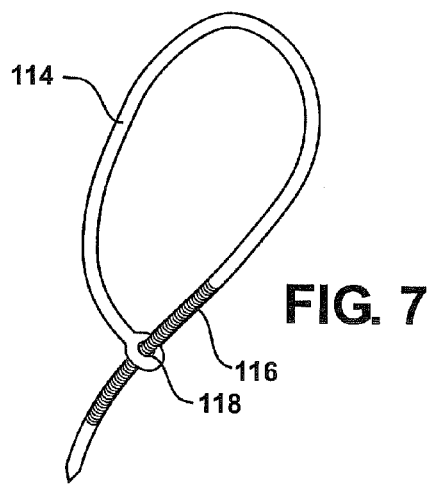
FIG. 7 is an illustration of a loop-shaped plastic support strap according to a further embodiment and by which an extending and serrated inserting portion insertably engages through an aperture defined in a remote end receiving portion.

Proceeding to FIG. 7, an illustration is provided of a loop-shaped plastic support strap 114 according to a further embodiment, and by which an extending and serrated inserting portion 116 integrally formed with the support strap is insertably engaged through an aperture 118 defined in a remote end receiving portion, thereby to establish a looped configuration for subsequent application about a damaged exterior bone location. As in previous embodiments, it is contemplated that the strap is pre-positioned in a first linear configuration about a damaged exterior location of a bone, following which the serrated portion 116 is inserted through the aperture location 118 and translated to a fully tightened position in which the defined loop is secured about the exterior damaged circumference of the associated bone (not shown).

Figure 7A:
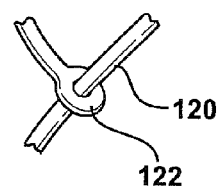
FIG. 7A is a partial illustration of a modified strap engagement configuration and by which a first substantially smooth edged extending portion is diameter dimensioned so as to be resistively seated through the apertured remote end receiving portion.
Figure 7B:
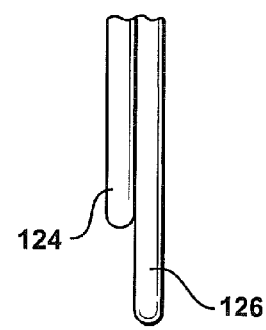
FIG. 7B is a further sectional illustration of a pair of extending plastic cables.
Figure 7C:
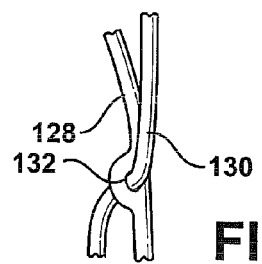
FIG. 7C is an alternate sectional configuration of first and second interengaging cables according to a yet further application.

FIG. 7A is a partial illustration of a modified strap engagement configuration and by which a first substantially smooth edged extending portion 120 is diameter dimensioned so as to be resistively seated through the apertured remote end receiving portion 122, the strap formed thereby maintaining its anchoring properties by virtue of a resistance fitting relationship established between the extending and receiving portion. In contrast to the arrangement shown in FIG. 7, the resistive holding forces established between the looped engaging portions substitute for a serrated (zip-strip) style engagement. FIG. 7B is a further sectional illustration of a pair of extending plastic cables 124 and 126 in end-sectioned and overlapping fashion, whereas FIG. 7C is an alternate sectional configuration of first 128 and second 130 interengaging cables according to a yet further application and by which the pair of composite cables exhibit an inter-engagement scenario illustrating an intermediate positioned apertured location 132 for receiving a threading end of the selected cable 130 and in order to create a desired resistive engagement about an exterior (e.g. cracked or otherwise damaged) bone surface.

Figure 8:
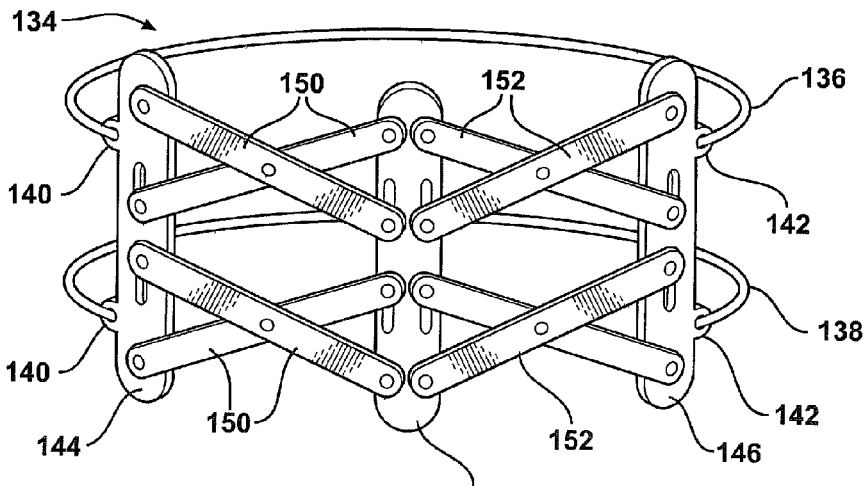
FIG. 8 is an illustration of a brace similar in regards to that illustrated in FIG. 3 and by which the encircling straps are secured to projecting end tabs associated with an outer-most pair of the extending supports, and again in addition to the plurality of tie or cable secured supports interengaged in circumferentially displaceable fashion along the straps by pluralities of crosswise extending scissor portions.

Referring now to FIG. 8, an illustration is provided of a brace 134 similar in regards to that illustrated in FIG. 3 and by which a pair of encircling straps 136 and 138 are secured to projecting end tabs (see opposite located pairs of tabs 140 and 142) associated with an outer-most pair, further at 144 and 146, of extending supports. An intermediately positioned support 148 is positioned between outer supports 144 and 146 and, in addition to the plurality of tie or cable secured outer supports 144 and 146, are interengaged in circumferentially displaceable fashion along the straps 136 and 138 by pluralities of crosswise extending scissor portions 150 and 152. The brace configuration 134 of FIG. 8 otherwise is largely repetitive to that shown at 34 in FIG. 3, both as to its construction and potential alternative configuration and with the exception that the generally more exposed configuration of the end disposed tabs 140 and 142 relative to the strap end mounting configuration renders possible the ability to establish additional tightening/tensioning configurations when installed over a damaged bone area.

Figure 9A:
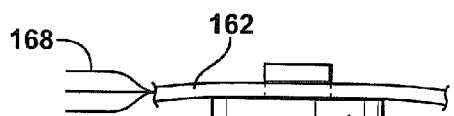
FIG. 9A is a partial view of an abutting location associated with a selected strap.
Figure 9:
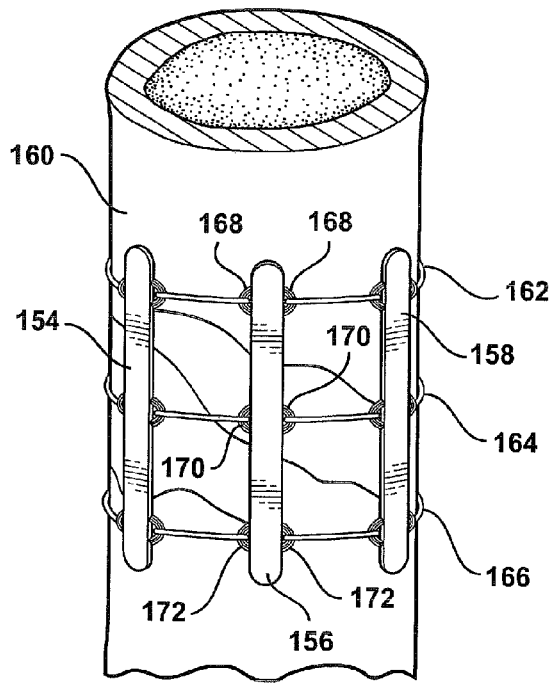
FIG. 9 is an environmental perspective of a bone engagement application according to a yet further embodiment, and by which a plurality of linear extending plastic supports, such as constructed of a composite plastic support which can also incorporate a graphite/carbon fiber mixture abuttingly engaged about linear extending and exterior periphery locations associated with the bone.
Figure 9B:
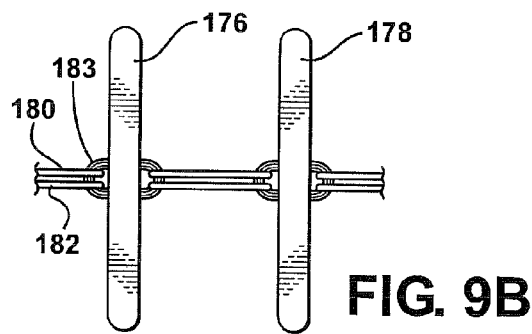
FIG. 9B is a partial view of a pair of alternately configured supports secured to one or more peripheral extending cables.
Figure 9C:
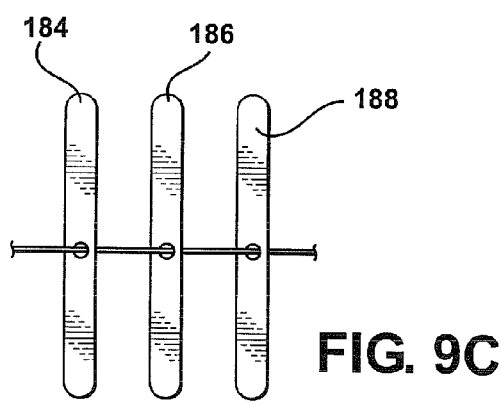
FIG. 9C is a partial view of a plurality of further configured supports secured by a single peripheral extending cable.

Referring to FIG. 9C, an environmental perspective is shown of a bone engagement application according to a yet further embodiment, and by which a plurality of linear extending plastic supports, see at 154, 156 and 158, each of which further capable of being constructed of a composite including any one or more of plastic/metallic/carbon material mixtures. As shown, the supports 154, 156 and 158 are abuttingly engaged about linear extending and exterior peripheral locations associated with a bone 160. To this end, a plurality of three encircling straps or bands are shown at 162, 164 and 166, these engaging through top, intermediate and lower linear locations of the supports and in order to apply as a desired and elongated exterior bone overlaying brace.

As with previous disclosed variants, the bands can be individually or collectively tightened to achieve a desired degree of tensioning/compressive outer surface support to the exterior bone location. It is additionally envisioned that graphite fibers (e.g. at 168, 170 and 172) can be employed, these being disposed either inside interior channels incorporated into the straps or in communicating fashion with the straps and which extend from seating locations of each strap 162, 164 and 166. The fibers can be tightened, such as by gripping a trailing end thereof and in order to further draw together or tighten the straps and associated supports to inwardly bias the same and further establish a protective cocoon about a damaged bone location exhibited by stress or fracture locations.

Referring now to FIG. 9A, a partial and crosswise cutaway view is shown of an abutting location established between a support, see at 174, associated with a selected strap, e.g. and 162, and through which extend graphite threads 168. FIG. 9B is a partial view of a pair of alternately configured supports 176 and 178, each being secured to one or more peripheral extending cables 180 and 182 (these further possibly including graphite threads or other tightening elements as representatively shown at 183 extending in cooperative fashion between the spaced apart cables and a selected mounting location to the support 176), and which are manipulated for drawing the supports together in a desired application. FIG. 9B is a partial view of a plurality of further configured supports 184, 186 and 188 secured by a single peripheral extending (and tightenable) cable 190 according to a further application. Although not shown, it is envisioned that additional anchors and the like can be mounted through end locations associated with each surface applied support 184-188.

Figure 9D:
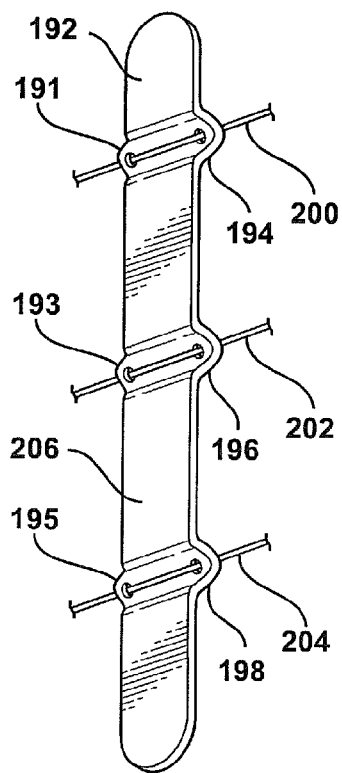
FIG. 9D is a sectional illustration of a selected composite plastic support exhibiting an inner facing and reduced profile for easing patient implantation and associated experienced pain.
Figure 9E:
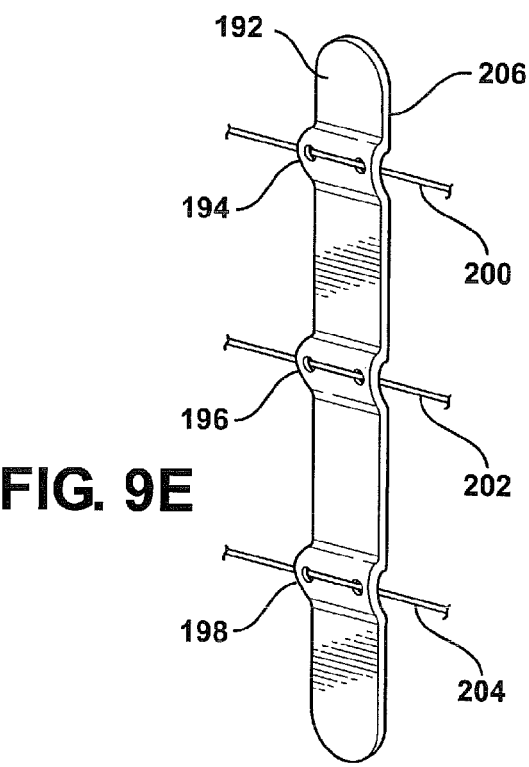
FIG. 9E is a rotated perspective of the composite plastic support shown in FIG. 9D.

FIG. 9D is a sectional illustration of a selected composite and elongated plastic support 192 exhibiting a modified three dimensional shape, see recess defining bend portions 191, 193 and 195 formed at intermediate spaced locations along the support 192, this resulting in the creation of inner facing and reduced area profiles for easing patient implantation and associated experienced pain. As also shown in the corresponding rotated perspective of FIG. 9E, a plurality of reinforced exterior projecting portions, at 194, 196 and 198 are created on opposite sides of the recess defined bend portions 191, 193 and 195, each defining a laterally (widthwise) projecting aperture through which is seated an associate cable (with or without associated graphite threads) and as representatively shown at 200, 202 and 204. The concept being the configuration of FIGS. 9D and 9E is to provide a substantially smooth and inner abutting surface 206 (see again FIG. 9D) when applied against an exterior of the bone, thereby reducing patient discomfort associated with rivet installation or anchoring (not shown in this view) and as further facilitated by the tightening (or tensioning) of the straps/strands associated with the supports.

Figure 10:
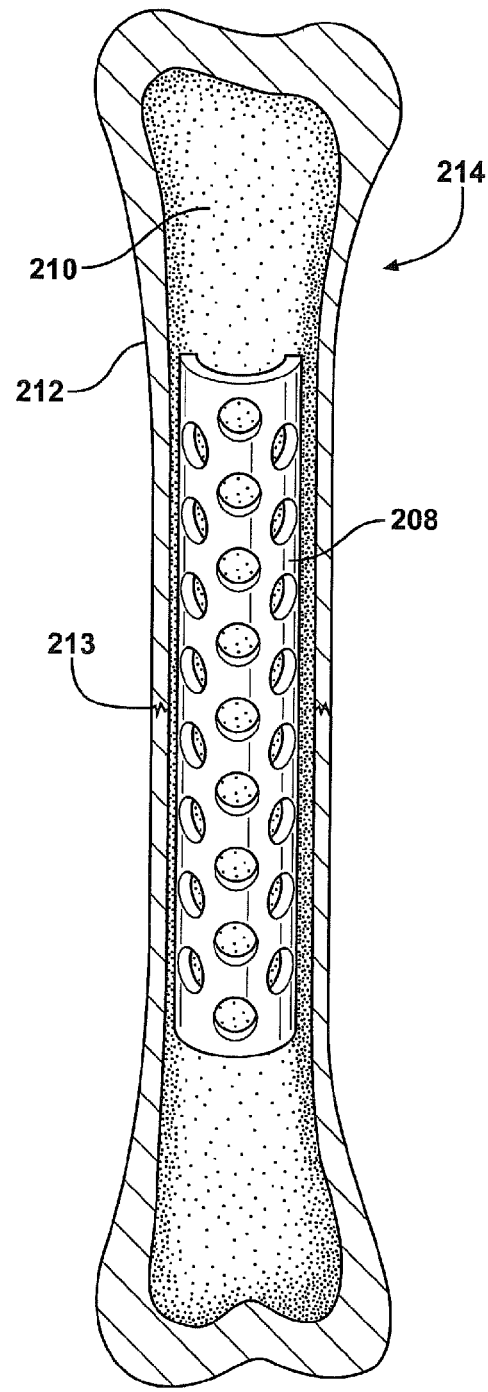
FIG. 10 is a cutaway illustration of a further preferred embodiment and in which a composite hardened plastic insert is supported within a hollow interior cavity associated with a fractured bone via an end configured insert channel defined in the bone.

FIG. 10 is a cutaway illustration of a further preferred embodiment and in which a composite hardened plastic insert 208 is supported within a hollow interior cavity 210 associated with a fractured bone 212 (see also break location 213), defined in the bone 212. FIG. 11 is an enlarged illustration of the insert 208 and which is interiorly hollowed with open first and second ends and along with multiple apertures 209 defined within its sleeve shaped wall, such as which can be constructed of a composite and hardened plastic material. The provision of the hollow ends and multiple apertures facilitate the flow through of inner bone marrow and the formation of new bone, such that the insert 208 can define a permanent part of the repaired bone. Although not shown, it is envisioned and understood that the stem shaped insert 208 can be installed such as through a section end of the bone.

Referring now to FIG. 12A, an illustration is shown at 216 of a first configuration of bone drill bit, such as which can be utilized in a kit or assembly including any one or more of the variants of bone supporting braces as described herein. The bit 216 is utilized in the anchoring of a mounting screw, and such as which incorporates a fluted section 218 defined along an intermediate length of the shaft. The purpose of the bit 216 is to establish an exterior surface proximate dovetail portion relative to a bone surface. As will be subsequently described, alternately configured bits contemplate the ability to form undercut portions within the bone.

FIG. 12B is an illustration at 220 of a reamer type bit according to a further possible configuration and which is provided for creating a successively larger diameter hole in a direction towards an exterior bone surface. FIGS. 13A-13E successively illustrate a variety of anchor screws exhibiting varying fluted and spike patterns, and which are respectively shown at 222, 224, 226, 228 and 230. The spike 222 exhibits a fairly consistent diameter, whereas that shown at 224 is tapered such that it corresponds with a mounting pattern created by the reamer drill bit 220 in FIG. 12B. Spike 226 exhibits angled retention tangs, whereas spike 228 exhibits a general spiral and minimal surface projecting thread pattern. Spike pattern 230 includes a lower minimally threaded configuration (see similar to that shown at 228) with an upper and head end proximate enhanced thread pattern (see at 232) for achieving additional gripping force.

Figure 14A:
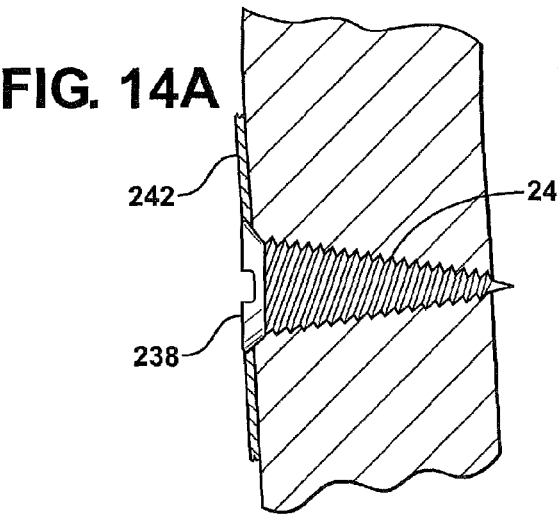
FIG. 14A is a cutaway illustration of a tapered bone aperture drilled by such as a reamer type bit and within which is anchored a suitably configured screw.
Figure 14B:
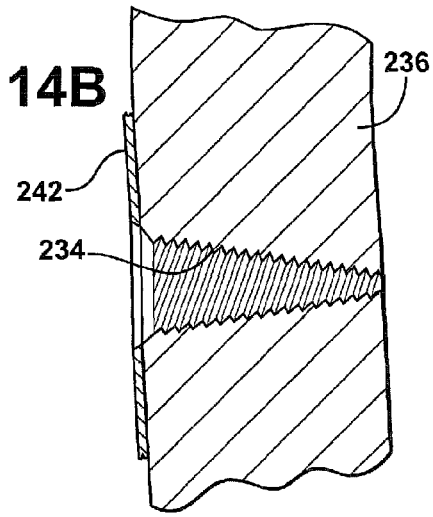
FIG. 14B illustrates a similar cutaway depicting a tapered screw surface according to a slightly different surface profile.

FIGS. 14A and 14B are cutaway illustrations of a series of tapered bone apertures, see selected surface 234 within bone 236, and which is drilled by such as a reamer type bit 220. Selected screw 238 (similar to that previously shown at 224 in FIG. 13B) is provided for and which is anchored within a further defined aperture 240 and for mounting a given exterior positioned location (see at 242) of a strap, band or plate shaped bracing support, such as according to any of the embodiments previously described. FIG. 14B further shows tapered surface 234 for seating screw 238 according to a slightly different configuration.

Figure 15A:
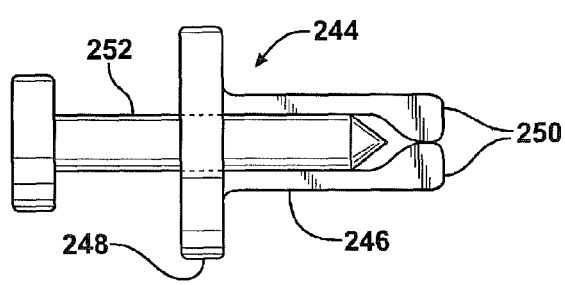
FIG. 15A is a side illustration of a combination anchor and collar shaped plastic spacer.
Figure 15B:
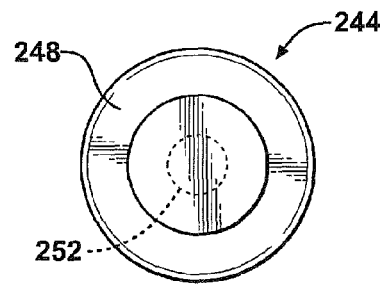
FIG. 15B is an end view of the anchor and plastic spacer of FIG. 15A.

FIG. 15A is a side illustration and FIG. 15B a corresponding end view of a combination anchor and collar shaped plastic spacer, see as generally shown at 244. The collar and anchor arrangement is functionally similar to that previously described in reference to the anchor rivet in FIG. 5B and by which a surface located brace or support (not shown) is fixedly secured in location relative to a damaged bone and includes an aperture which is in alignment with a hole in the bone, such further incorporating a desired undercut profile.

As best shown in FIG. 15A, the spacer is shown in cutaway and includes a general sleeve shaped and internally hollowed passageway, as shown at 246, a first exterior end of the passageway including an annular projecting end 248 (or disc shaped portion) sandwiching a location of a plate or brace (see at 247 in FIGS. 16B and 16C) over an exposed surface of a bone 249. The sleeve shaped and passageway defining portion, as shown in cutaway, further exhibits (as can only be shown by lineal cut away as in each of FIGS. 15A, 16B and 16C) an inner end disposed and inwardly radially projecting enlargement, see at 250.

Figure 16A:
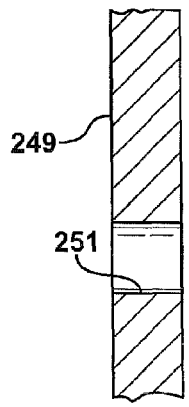
FIG. 16A is an illustration of an initially drilled condition of a bone in preparation for receiving a combination anchor and plastic spacer associated with a surface securing brace.
Figure 16B:
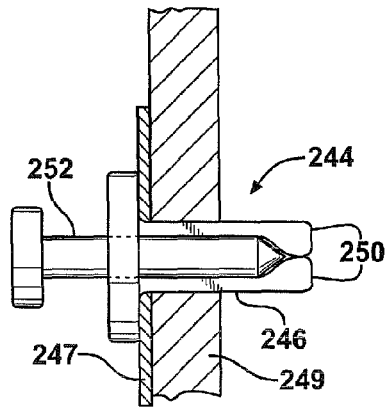
FIG. 16B is a succeeding illustration showing the anchor and plastic spacer in initially positioned and pre-installed fashion.
Figure 16C:
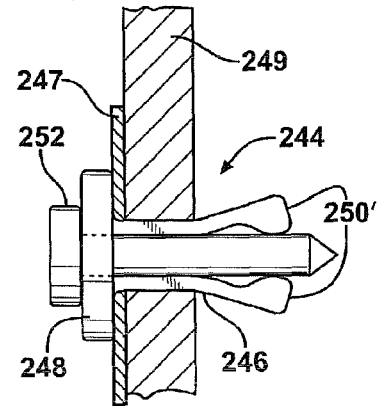
FIG. 16C is a succeeding installation condition and showing the anchor displacing through the plastic collar spacer, causing the spacer to deform and grip about both inner and outer annular edge surfaces associated with the drilled hole and to secure the brace in adhering fashion to the surface of the bone.

As further referenced at FIG. 16A, an illustration is provided of an initially drilled condition, see aperture wall 251, of the bone 249 in preparation for receiving a combination anchor and plastic spacer associated with a surface securing brace. FIG. 16B is a succeeding illustration showing the anchor 246 with plastic spacer in initially positioned and pre-installed fashion relative to the bone aperture 251 and with an inner spike 252 in pre-positioned fashion relative to the inner passageway and projecting from the enlarged disk end 248. Finally, FIG. 16C is a succeeding installation condition and showing the spike 252 inwardly displacing through the plastic collar spacer, causing the spacer, and in particular its inner end and radially inwardly positioned enlargement to deform (see as further shown at 250') and grip about the inner annular edge surface associated with the drilled hole, concurrent with the disk 248 being drawn against the exterior surface of the bone 249 surrounding the drilled hole in biasing fashion, and to thereby secure the sandwiched brace 247 in adhering fashion to the exterior surface of the bone 249.

Referring now to FIG. 17A, a side cutaway illustration is shown of a mounting screw 254 for mounting a brace plate 256 to a surface of a bone 258. As shown, the brace plate 256 can include a dovetail shaped aperture as shown in lineal cutaway and to assist in flush seating of a likewise tapered configuration associated with a head of the screw 254.

FIG. 17B is a further illustration of a modified anchor and deformable spacer, as generally shown at 260, for mounting a further version of brace plate 262 to the bone 258. Along with the alternate modified anchor 264 shown in lineal cutaway in FIG. 17C, each of the anchor configurations 260 and 264 are similar in construction and application to that shown at 244 in FIG. 15, with the exception that the elastic and deformable configuration of the surrounding collars, along with their inner configured ends, can be modified in order to vary the anchoring properties relative to the inner bone surfaces proximate the drilled hole. This is further referenced by the modified and end-flared pattern 266 exhibited by the inwardly disposed and deformable covering 266 in FIG. 17B, as well as is further shown by the alternately configured and outwardly angled pattern, at 268, in FIG. 17C, and which provides another version of anchoring to the inner bone surface.

Referring now to FIGS. 18A-18C, a succession first closed and second open end views are shown of a laterally displaceable anchoring screw for seating in an undercut bone aperture. Specifically, and as is further shown by the perspective view of FIG. 18C, the anchoring screw includes a plurality of individual and linearly extending portions, see in the illustrated example as shown by four individual portions 270, 272, 274 and 276 associated with the anchoring screw and which are outwardly displaced relative to a central supporting and rotatable trigger 278. Other pluralities of laterally displaceable portions, including such as two, three or other, are also envisioned.

A turn key aperture (see at 279) can be designed into a top exposed location of the trigger 278, such as which can be accessed by a surgeons key (not shown) and which is configured in order to outwardly and laterally displace the individual portions 270-276 in the fashion shown and once the anchor screw has been pre-installed within a specified and pre-machined bone location.

The laterally displaceable portions 270-276 can further be provided as top mounted disks secured atop an integrally formed screw body 281. Although not shown, the hidden undersides of the disk portions can be secured through a pin and slot or other arrangement permitting them to be laterally displaced in the manner shown in FIG. 18B. Although not shown, a cam profile can further be established between the key accessed trigger 278 and the opposing/aligning surfaces of the disk portions, such as to facilitate when being expanded and locked in the position 18B (and whereby they fully seat within a recess undercut profile defined in the bone after being pre-inserted.) It is further understood that the anchoring screw can be redesigned, and such that redesigned outwardly displaceable portions do not extend an entire length of the anchor but are limited in location to either or both inner and outer most ends of a redesigned anchor (see as generally shown at 280 in FIG. 18D). A turn key access location, see as shown at 282, can be connected to an internal and rotatable stem (not shown) defined within the body of the anchor and which can likewise be engaged to outwardly displace upper 284 and lower 286 end positioned enlargements, these in turn seating within undercut positioned recesses defined in a hole previously drilled in a bone location.

FIG. 19A is a further illustration of an anchoring screw and which incorporates a plasticized sleeve 288, within which are disposed a pair of internal passageway proximate and laterally displaceable undercut engaging portions 290 and 292 (this being further illustrated in the transparent view of FIG. 19C showing the anchoring sleeve 288 and illustrating both the configuration of the inner passageway communicating (at 289) and laterally displaceable undercut engaging portions 290 and 292, as well as the deformable properties associated with the circumferential location 294 of the sleeve overlaying the undercut portions. FIG. 19B is a succeeding illustration to that shown in FIG. 19A and depicting the undercut engaging portions 290 and 292 (which can exhibit ally of a disk or semi-spherical ball shape) laterally outwardly bulged/displaced as illustrated by the surface deformed sleeve location 294, this again in response to the inwardly engagement of an associated anchoring screw 294. The laterally deformable sleeve 288 can include the undercut engaging portions 290 and 292 arranged at any linear position in proximity to its inner passageway (as further shown in FIG. 19C) and so as to correspond to any desired undercut mounting arrangement within a bone. The undercut engaging portions 290 and 292 each further include inner configured ramps or angled surfaces, at 296, for promoting outwardly displacement in response to being contacted by a pointed end associated with the inwardly displaced spike 294.

Figure 21A:
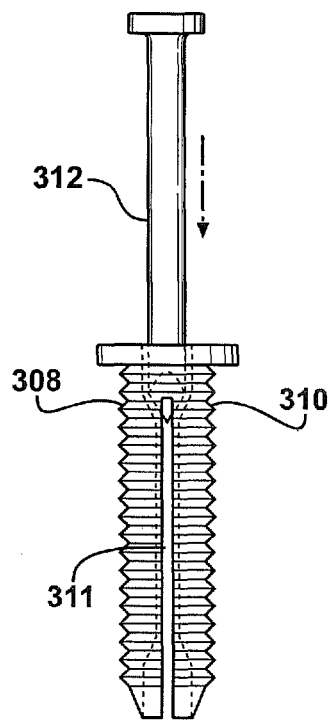
FIG. 21A is an illustration of a yet further configuration of anchoring sleeve and exhibiting first and second laterally displaceable halves which are actuated via an inwardly engaging spike.
Figure 21B:
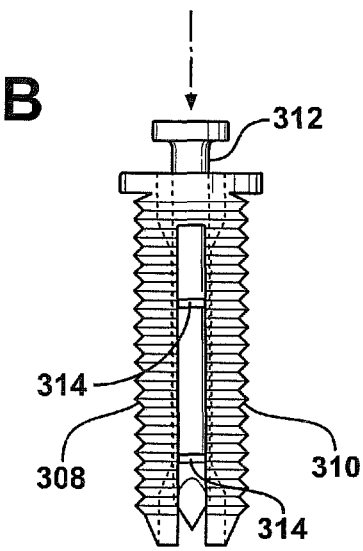
FIG. 21B is a succeeding illustration in which the first and second linearly extending sleeve halves are shown in laterally displaced fashion and inter-supported by a combination of the inwardly displaced spike and widthwise interconnecting and sliding collar portions.

A modified of anchoring screw is shown at FIG. 20A and which exhibits a reconfigured sleeve 298 with first 300 and second 302 end extending and laterally displaceable portions. As further shown in FIG. 20B, a cutaway view of the anchoring screw shown in FIG. 20A illustrates one possible configuration of linkage, see interiorly narrowing and structurally weakened pivoting portions at 304 and 306 to which are associated with the laterally and inner end displaceable portions 300 and 302, for causing outwardly lateral deflection of the end extending sleeve portions 300 and 302 in response to inward engagement of the associated spike 306;

FIG. 21A is an illustration of a yet further configuration of anchoring sleeve and exhibiting first 308 and second 310 laterally displaceable halves separated by one or more linear extending and spacing slots 311, and which are actuated via an inwardly engaging spike 312. The passageway created between the slots 311 includes an expanded lower profile. As further shown in FIG. 21B a succeeding illustration to FIG. 21A is provided in which the first and second linearly extending sleeve halves 308 and 310 are shown in laterally displaced fashion and inter-supported by a combination of the inwardly displaced spike 312 (along with optional widthwise interconnecting and sliding collar portions 314 which extend through annular apertures defined in each of the halves 308 and 310) and in order to positionally support the sleeve during outward displacement of the halves 308 and 310. The bone wall also exerts an inward compressive force for anchoring the expanded collar in place. Although not shown, it is also envisioned that the support collars 314 can be substituted by a thin connecting membrane established between the laterally expandable halves 308 and 310, and which imparts a desired locating and compressive force to the displaceable halves.

Figure 22A:
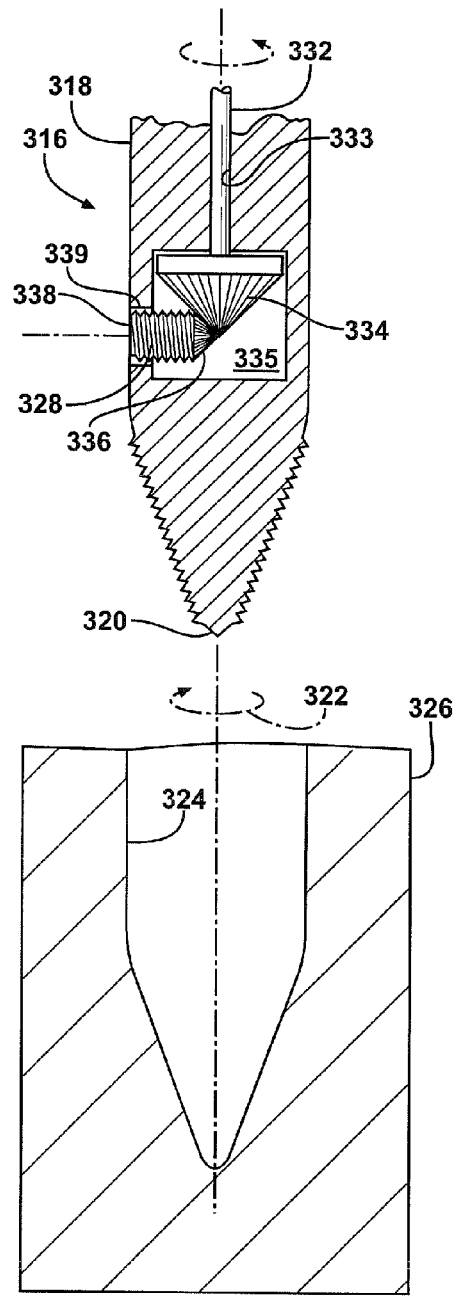
FIG. 22A is an exploded illustration of a modified drill bit according to a further preferred embodiment and which the bit drills a primary hole within the bone.

Referring to FIG. 22A, an exploded illustration is generally shown in cutaway at 316 of a modified drill bit according to a further preferred embodiment and according to an initial machining step in which the drill bit drills a primary anchor mounting hole within a bone location. The bit is shown in cutaway and is substantially solid with an outer wall 318 terminating in a pointed end 320 and which is rotated (see at 322) in order to create an initial aperture (see further wall 324) defined within a bone 326.

Figure 22B:
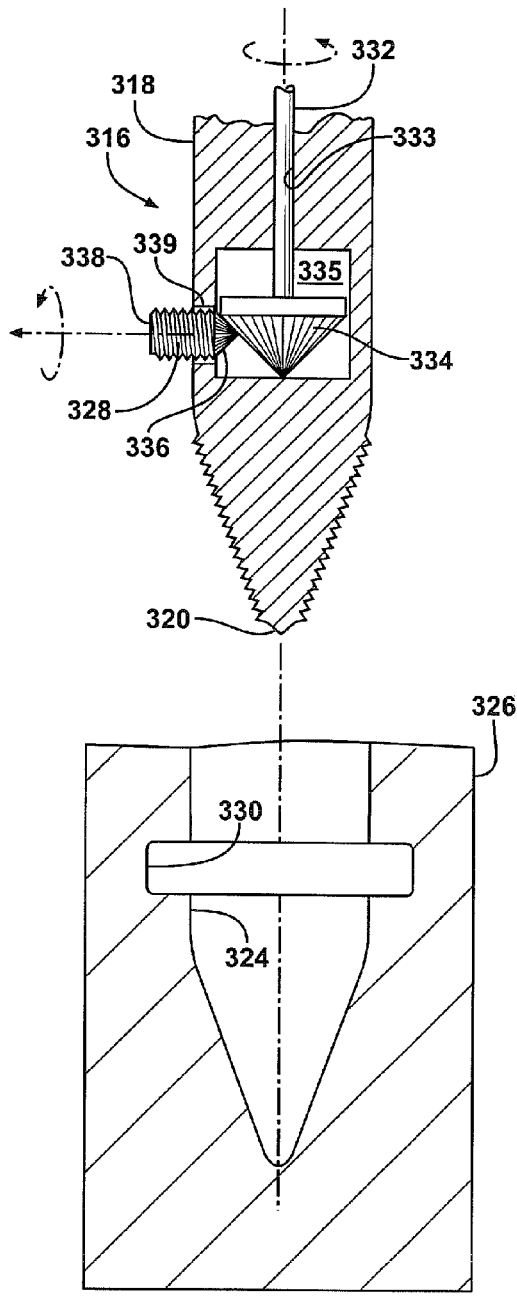
FIG. 22B is a succeeding illustration of the drill bit according to FIG. 22A, illustrating the deployment of a laterally redirected secondary bit for creating a desired bone undercut within a recessed location of the primary hole within the bone.

Referring again to FIG. 22A in combination with succeeding FIG. 22B, illustrated is the deployment of a laterally redirected secondary bit 328, such exhibiting a crosswise extending and rotatable screw shape, for creating a desired bone undercut profile 330 within a recessed location of the primary hole 324 within the bone 326. In one preferred variant, an inner supported and rotatable shaft or stem, see at 332, extends within an inner an lineal extending passageway 333 and terminates in a first lower end positioned bevel gear portion 334 which is seated within an upper portion of a three dimensional open interior (see at 335) defined within the drill bit 316.

The secondary bit 328 exhibits an integrally formed and inner end positioned secondary bevel gear portion 336 arranged in inter-meshing engagement with the first bevel gear 334. The secondary bit is further spring loaded or otherwise biased or mechanically retained in the position shown in FIG. 22A, such that the secondary bit 328 is seated in crosswise extending fashion relative to the elongate extending direction of the main tool bit 316 and the inner stem 332 driving the primary (first) bevel gear 334. Although not clearly show, the secondary bit 328 is typically seated within a crosswise extending sleeve or pocket, see as shown at 339 which communicates with the three dimensional open interior 335, such that the bit 328 is retained in position in FIG. 22A with an outer end face 338 of the secondary bit 328 retained substantially flush with the wall surface 318 of the drill bit.

As further shown in FIG. 22B, the primary bevel gear 334, as acted upon by the connecting stem 332, is both rotated and linearly and downwardly displaced toward a lower portion of the three dimensional open interior. In response to the combined rotational/translational force imparted by the primary bevel gear 334, the secondary engaged bevel gear 336 and integrally extending secondary bit 328 is caused to both rotate and to linearly displace laterally outwardly from the crosswise configured aperture 339 in the projecting fashion shown.

In a practical embodiment, the successive downward displacement of the primary bevel gear 334 and corresponding lateral outward displacement of the secondary gear 328 occurs progressively as a result of continuous and progressive wear within the bone location resulting in the undercut profile 330. In order to create the desired annular profile for the undercut 330 in FIG. 22B, the main drill bit 316 is slowly rotated one full and additional circumferential turn (360°), again following the creation of the initial drill hole 324, and concurrent with the undercut forming operation.

Figure 23:
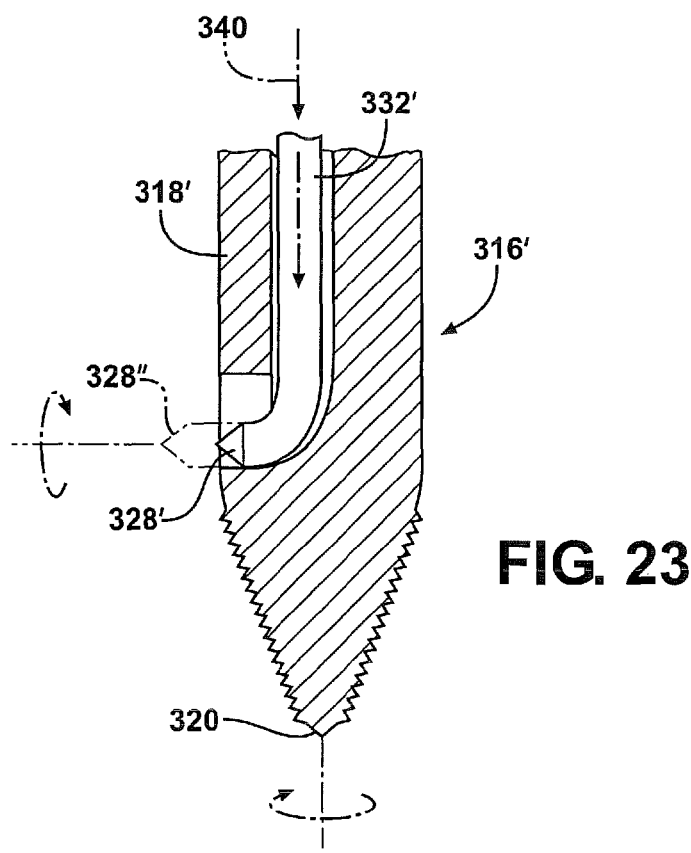
FIG. 23 is a modification of the bit illustrated in FIG. 22 and illustrates in cutaway a linearly flexible and torsionally rigid interior positioned stem such as constructed of a durable polymeric or other hybrid material and which terminates in a modified secondary bit end which relies upon an axial driving force exerted on the inner flexible and torsionally resistant stem in order to create the desired undercut pattern within a previously formed hole.

As finally shown in FIG. 23, a modification 316' of the bit illustrates a linearly flexible and torsionally rigid interior positioned stem 332' (such as constructed of a durable polymeric or other hybrid material) and which terminates in a modified secondary bit end 328'. In contrast to the bevel arrangement in FIG. 22, the modified version of FIG. 22A relies upon an axial driving force (see arrow 340) exerted on the inner flexible and torsionally resistant stem 332'.

In this fashion, the secondary bit 328' is caused to be progressively outwardly displaced (see as further shown in phantom at 328") concurrent with being rotated for undercut profile creation. As with the bit 316 in FIG. 22, the controlling spindle portion of the medical drill (not shown) can be configured so that, upon location and initiation of the secondary drill bit 328 or 328' (this again following the initial hole forming operation 324), the main drill bit is caused to slowly and progressively rotate about a single revolution in order to create the desired annular undercut pattern for subsequently receiving a likewise undercut seating bone anchor. Consistent with the description provided in preceding embodiments. the undercut profile 330 can be formed within an interior solid portion of a bone (again as shown at 326) or can be defined in a reverse dovetail relationship with an inner facing surface of a bone layer communicating with a hollow and bone marrow filled interior (see such as shown in each of FIGS. 4A, 5A and 5B).

Having described my invention, other and additional preferred embodiments will become apparent to those skilled in the art to which it pertains, and without deviating from the scope of the appended claims:

I claim:

1. A brace for supporting a circumferential exterior surface of a damaged bone, said brace comprising:
   a body adapted to being placed in encircling fashion about the circumferential exterior surface of the bone in overlapping fashion relative to a damaged location, said body including a plurality of flexible and elongated scissor portions, each having a flattened shape and being arranged as successive pairs which are interconnected at each of intermediate overlapping and end extending locations;
   said body further including an additional pair of elongated, parallel extending and end disposed supports which are pivotally interconnected to outermost opposite extending ends of said pairs of said scissor portions; and
   said body further including a pair of elongated ties seating through apertures formed in said end disposed supports such that said elongated ties interconnect said end supports and are adapted to extend about a remaining portion of the bone circumference not overlayed by said overlapping pairs of scissor portions;
   displacement of said ties relative to at least one of said end disposed supports causing said elongated members to inter-extend in scissor-like fashion and to spatially displace said end supports about the bone exterior in order to tighten said body against the bone and to apply a preferred degree of compressive and immobilizing force around its damaged exterior, incision or removal of said ties permitting said body to be removed from the bone.

2. The brace according to claim 1, said pairs of scissor portions further comprising first and second sub-pluralities of crosswise extending scissor portions interconnecting between said end disposed supports.

3. The brace according to claim 2, further comprising an intermediate support positioned between said end disposed supported and to which said sub-pluralities of crosswise extending pairs of scissor portions are additionally pivotally engaged.

4. The brace according to claim 1, further comprising at least one lengthwise extending slot defined in each of said end disposed supports and within which is both pivotally and displaceably seated a pivotal end location of a selected scissor portion in order to provide a degree of sliding displacement of said scissor portions along said end support to compensate for misalignment between said interconnected pairs of scissor portions.

5. The brace according to claim 1, each of said elongated scissor portions and said end supports further include a plasticized construction.

* * * * *